(12) United States Patent
Steinhardt et al.

(10) Patent No.: US 10,175,389 B2
(45) Date of Patent: *Jan. 8, 2019

(54) NON-CRYSTALLINE MATERIALS HAVING COMPLETE PHOTONIC, ELECTRONIC OR PHONONIC BAND GAPS

(71) Applicant: The Trustees of Princeton University, Princeton, NJ (US)

(72) Inventors: Paul J. Steinhardt, Princeton, NJ (US); Salvatore Torquato, Princeton, NJ (US); Marian Florescu, Guildford (GB)

(73) Assignee: The Trustees of Princeton University, Princeton, NJ (US)

(*) Notice: Subject to any disclaimer, the term of this patent is extended or adjusted under 35 U.S.C. 154(b) by 254 days.

This patent is subject to a terminal disclaimer.

(21) Appl. No.: 15/280,150

(22) Filed: Sep. 29, 2016

(65) Prior Publication Data

US 2017/0082780 A1 Mar. 23, 2017

Related U.S. Application Data

(60) Continuation of application No. 14/953,652, filed on Nov. 30, 2015, now Pat. No. 9,461,203, which is a (Continued)

(51) Int. Cl.
*H01L 33/16* (2010.01)
*H01L 33/00* (2010.01)
(Continued)

(52) U.S. Cl.
CPC .............. *G02B 1/005* (2013.01); *B82Y 20/00* (2013.01); *G01K 17/00* (2013.01); *G01L 1/24* (2013.01);
(Continued)

(58) Field of Classification Search
CPC .. G02B 1/005; G02B 27/0012; G02B 5/3025; B82Y 20/00
See application file for complete search history.

(56) References Cited

PUBLICATIONS

Obioma U. Uche, Frank H. Stillinger, and Salvatore Torquato,Constraints on collective density variables: Two dimensions, Physical Review E 70, 046122 (2004), © 2004 The American Physical Society.*

(Continued)

*Primary Examiner* — Bijan Ahvazi
(74) *Attorney, Agent, or Firm* — Medlen & Carroll, LLP

(57) ABSTRACT

The invention provides an article of manufacture, and methods of designing and making the article. The article permits or prohibits waves of energy, especially photonic/electromagnetic energy, to propagate through it, depending on the energy band gaps built into it. The structure of the article may be reduced to a pattern of points having a hyperuniform distribution. The point-pattern may exhibit a crystalline symmetry, a quasicrystalline symmetry or may be aperiodic. In some embodiments, the point pattern exhibits no long-range order. Preferably, the point-pattern is isotropic. In all embodiments, the article has a complete, TE- and TM-optimized band-gap. The extraordinary transmission phenomena found in the disordered hyperuniform photonic structures of the invention find use in optical micro-circuitry (all-optical, electronic or thermal switching of the transmission), near-field optical probing, thermophotovoltaics, and energy-efficient incandescent sources.

4 Claims, 12 Drawing Sheets

Related U.S. Application Data division of application No. 13/379,740, filed as application No. PCT/US2010/039516 on Jun. 22, 2010, now Pat. No. 9,207,357.

(60) Provisional application No. 61/269,268, filed on Jun. 22, 2009.

(51) Int. Cl.
| | |
|---|---|
| *G02B 1/00* | (2006.01) |
| *B82Y 20/00* | (2011.01) |
| *G01K 17/00* | (2006.01) |
| *G01L 1/24* | (2006.01) |
| *G01N 21/17* | (2006.01) |
| *G02B 6/122* | (2006.01) |
| *G02B 6/125* | (2006.01) |
| *G02B 5/30* | (2006.01) |
| *G02B 27/00* | (2006.01) |
| *H01B 1/00* | (2006.01) |
| *H01B 1/12* | (2006.01) |

(52) U.S. Cl.
CPC ........... *G01N 21/17* (2013.01); *G02B 5/3025* (2013.01); *G02B 6/125* (2013.01); *G02B 6/1225* (2013.01); *G02B 27/0012* (2013.01); *H01L 33/0058* (2013.01); *H01L 33/0095* (2013.01); *H01L 33/16* (2013.01); *Y10T 29/49993* (2015.01)

(56) References Cited

PUBLICATIONS

Keiichi Edagawa, Satoshi Kanoko, and Masaya Notomi, Photonic Amorphous Diamond Structure with a 3D Photonic Band Gap, Physical Review Letters, PRL 100, 013901 (2008), © 2008 The American Physical Society.*

Chongjun Jin, Xiaodong Meng, Bingying Cheng, Zhaolin Li, and Daozhong Zhang, Photonic gap in amorphous photonic materials, Physical Review B, vol. 63, 195107, © 2001 The American Physical Society.*

* cited by examiner

The concentric ring identified by the arrow arises in the image because of a TE photonic band gap in the structure.

ically crystals to symmetries that do not lend themselves to dielectric materials other than those with dielectric constants that produce very high dielectric contrast. For many applications, furthermore, the band gaps in periodic structures tend to be of limited usefulness because their anisotropy makes devices made with them highly direction-dependent. Periodicity also limits the engineer to a narrow choice of defects, and increases the risk of introducing unintended defects during fabrication. These periodicity-induced limitations apply also to structures sized to control the passage of phonons and electrons.

NON-CRYSTALLINE MATERIALS HAVING COMPLETE PHOTONIC, ELECTRONIC OR PHONONIC BAND GAPS

This application is a Continuation of, and claims priority to, co-pending U.S. patent application Ser. No. 14/953,652, filed Nov. 30, 2015, which claims priority to U.S. patent application Ser. No. 13/379,740, filed Feb. 15, 2012, which is a national entry of PCT/US2010/039516, filed Jun. 22, 2010, which claims priority to Provisional Application Ser. No. 61/269,268, filed Jun. 22, 2009, the contents of which are incorporated herein in their entirety.

STATEMENT REGARDING FEDERALLY SPONSORED RESEARCH OR DEVELOPMENT

This invention was made with government support under Grant No. DMR-0606415 awarded by the National Science Foundation. The government has certain rights in the invention.

Materials are needed that relax constraints imposed by periodicity but allow the artisan to engineer complete band gaps that preferably do not depend on direction or polarization.

SUMMARY

In various embodiments, the invention provides articles of manufacture, and methods of designing and making said articles, wherein the article comprises a plurality of material-elements disposed with respect to one another as a heterostructure preferably in a non-crystalline or quasicrystalline, hyperuniform, isotropic distribution in a condensed or solid state. Articles that embody the invention permit excitations in the form of waves of energy to propagate through them or, depending upon the frequency of the wave and its direction of propagation, prohibit such passage by reflection or trapping. Additionally, said articles have a complete band gap, preferably TE- and TM-optimized.

FIELD

Embodiments of the invention relate to materials having photonic, electronic or phononic band gaps, methods of designing such materials, and devices that comprise them.

BACKGROUND

Crystals are materials composed of elements arranged in a repetitive order that confers on the overall structure a wavelike configuration. These "waves" tend to interact with wavelike excitations traversing such structures. For example, propagation of a vibration through such a structure, although not straightforward, can be fully and predictably described (as a phonon) given sufficient knowledge of the wave-structure of the material. Photonic crystals comprise two or more periodically repeating dielectric materials with which photons (i.e., electromagnetic waves, which is the more straightforward choice of name for the wave/particle duality in this context) interact according to the laws of refraction that apply to electromagnetic waves according to Maxwell's equations. Photonic crystals have numerous applications as efficient radiation sources, sensors and optical computer chips.

A consequence of the repetitious structure of photonic crystals is that light of certain wavelengths (or "frequencies," the reciprocal of wavelength) traveling in certain directions and orientations (or "polarizations") will not propagate through the crystal. That is, across the entire spectrum of wavelengths, certain frequency ranges (or "bands") cannot pass through the structure. The transmitted spectrum thus has "gaps" in it. In common parlance, the property of the structure that gives rise to a gap in the transmitted spectrum is called a "band gap." Band gaps that reject a band of frequencies no matter their direction or polarization are called "complete band gaps." The utility of such band gaps, like the electronic band gaps in semiconductors, lies in their susceptibility to being breached by defects intentionally introduced into the structure. By violating the perfect periodic arrangement of the dielectric material-elements of the crystal, a previously prohibited frequency band is allowed passage into the crystal, where it may be trapped, re-directed, or otherwise altered.

The usefulness of the complete band gaps in periodic structures is, however, limited by the very periodicity on which they depend. Periodicity limits the engineer of pho- In preferred embodiments, the article comprises a non-crystalline, hyperuniform heterostructure comprising a plurality of material-elements and a complete band gap. In one embodiment, said heterostructure is derived from a hyperuniform pattern of points. In one embodiment, said point-pattern comprises a plurality of points disposed in a plane. In another embodiment, said point-pattern comprises a plurality of points disposed in a d-dimensional space to create a d-dimensional point-pattern. In one embodiment, said heterostructure is a polygonal heterostructure. In one embodiment, said heterostructure is a polygonal heterostructure having an azimuthal symmetry. In another embodiment, said heterostructure is a polyhedral heterostructure. In one embodiment, said heterostructure exhibits a quasicrystalline symmetry. In one embodiment, said heterostructure comprises material-elements arranged with a long-range order. In another embodiment, said heterostructure comprises disordered material-elements. In one embodiment, said heterostructure is translationally isotropic. In one embodiment, said heterostructure is rotationally isotropic. In one embodiment, said material-elements of said heterostructure comprise a lattice, said lattice comprising a plurality of polygonal cells, wherein a plurality of intersecting lines defines said polygonal cells, said lines define cell-edges, said intersections define vertices, and each said cell defines therein a polygonal cell-space. In another embodiment, said lattice comprises a plurality of polyhedral cells, wherein said plurality of intersecting lines defines said polyhedral cells, wherein each said cell comprises a plurality of faces, a plurality of vertices and defines therein a polyhedral cell-space.

In one embodiment, said edges, faces and vertices have disposed thereon a first material-element, and said cell-spaces are filled with a second material-element. In one embodiment, said first material-element has a higher dielectric constant than said second material element. In a preferred embodiment, said first material-element comprises silicon, and said second material-element comprises air. Further, in this embodiment, said first material-element is disposed on said edges or said faces at finite thickness and each said vertex is coincident with a centroid of a cylinder having a finite thickness and a finite radius.

In one embodiment, the invention provides a method of making a hyperuniform heterostructure having a complete band gap comprising the steps of:
 i) selecting a structure factor for said heterostructure,
 ii) constructing a box of size L, said box having a first point-pattern of points, wherein said points are spaced apart in a translationally disordered manner, said spaced-apart points having an average spacing, wherein said average spacing is <<L,
 iii) constructing a Delaunay trivalent tiling from said first point-pattern and plotting a centroid for each said tile to create a centroid point-pattern,
 iv) identifying for each centroid in said centroid point-pattern a nearest-neighbor neighborhood of said tile;
 v) constructing a plurality of lines to connect said centroids in each said neighborhood in such a manner that (i) said plurality of lines defines a plurality of edges or faces having vertices, (ii) said plurality of edges or faces defines a super-cell having therein a cell-space, and (iii) each said super-cell surrounds an unique point in said first point-pattern;
 vi) constructing a heterostructure by disposing on said edges or faces and vertices a first material-element and filling said cell-spaces with a second material-element, and assembling said heterostructure from a plurality of said supercells.

In one embodiment, said first point-pattern of said method comprises vertices of a Penrose tiling.

In a preferred embodiment, said first point-pattern of said method has a parameter $\chi$ that determines a fraction of wavenumbers k within a Brillouin zone for which the structure factor S(k) is set equal to zero such that, as $\chi$ increases, $k_c$ increases until $\chi$ reaches a critical value $\chi_c$, beyond which said disordered pattern attains a long-range translational order.

In one embodiment, said first material-element of said method has a higher dielectric constant than said second material element. In a preferred embodiment, said first material-element comprises silicon, and said second material-element comprises air. Further, in this embodiment, said first material-element is disposed on said edges or faces at a finite thickness and each said vertex is coincident with a centroid of a cylinder having a finite thickness and a finite radius.

In a preferred embodiment, said centroid point-pattern exhibits a number variance $\langle N_R^2 \rangle - \langle N_R \rangle^2 \propto R^p$, within a spherical sampling window of radius R, wherein p<d.

DEFINITIONS

Figure 1:
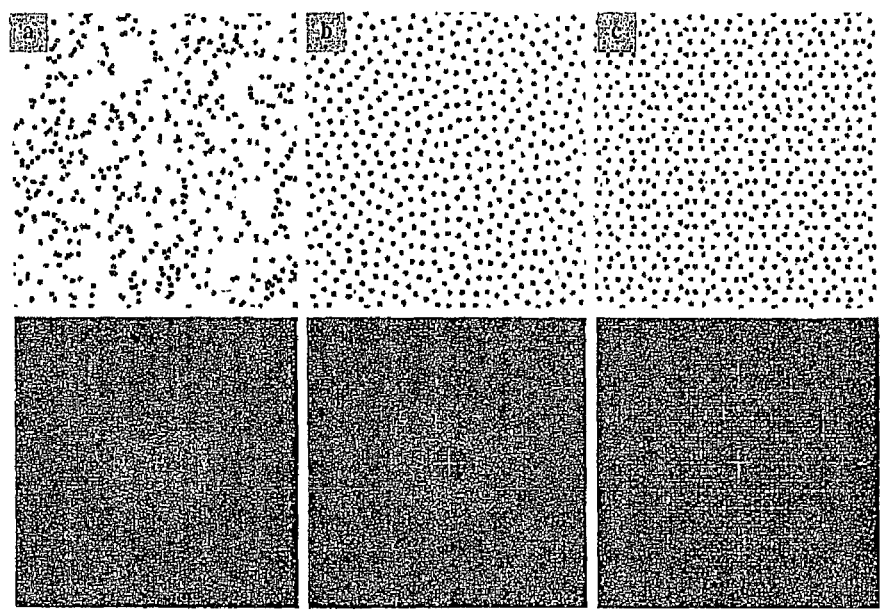
FIG. 1 provides point-patterns and diffraction images of the scattering function S(k) for structures having (a) an isotropic but non-hyperuniform distribution of scattering elements, (b) an isotropic, hyperuniform but disordered distribution, and (c) an anisotropic, hyperuniform distribution with five-fold symmetry (a quasicrystalline pattern).

To facilitate an understanding of the various embodiments of this invention, a number of terms (which may be set off in quotation marks in this Definitions section) are defined below. Terms defined herein (unless otherwise specified) have meanings as commonly understood by a person of ordinary skill in the areas relevant to the present invention. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, but the usage of any particular term does not delimit the invention, except as outlined in the claims.

The phrase "chosen from A, B, and C" and the like, as used herein, means selecting one or more of A, B, C.

As used herein, absent an express indication to the contrary, the term "or" when used in the expression "A or B," where A and B refer to a composition, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of a, c, and b; c, b, and a, and c, a, and b, etc.

Unless otherwise indicated, all numbers expressing quantities of ingredients, properties such as molecular weights, reaction conditions, etc., as used in the specification and claims, are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not," when preceding and made in reference to any particular named composition or phenomenon, means that only the particularly named composition or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "increase," "elevate," "raise," and grammatical equivalents when used in reference to the level of a substance and/or phenomenon in a first instance relative to a second instance, mean that the quantity of the substance and/or phenomenon in the first instance is higher than in the second instance by any amount that is statistically significant using any art-accepted statistical method of analysis. The increase may be determined subjectively, when a person refers to his subjective perception of pain, etc., for example, or objectively, when a person's observable behavior indicates pain. Correspondingly, the terms "reduce," "inhibit," "diminish," "suppress," "decrease," and grammatical equivalents when used in reference to the level of a substance and/or phenomenon in a first instance relative to a second instance, mean that the quantity of substance and/or phenomenon in the first instance is lower than in the second instance by any amount that is statistically significant using any art-accepted statistical method of analysis.

A number of the terms used herein are defined in geometry. Some embodiments of the invention, for example, relate to the "construction" of geometrical figures, whether with pencil, paper and compass or by means of computer programs, as distinct from the "construction" of objects, systems, etc. with physical materials. The term may be used herein in both senses, and its meaning in any instance will be determined by the context. A constructed "line" herein may be straight, curved, continuous, discontinuous or segmented, signifying connectedness, direction, segregation, etc. as the context so admits. Various geometrical forms such as but not limited to "triangle," "trihedron," "box," "face," "wall," "cell," "locus," "point," "centroid," and "cylinder" are referred to herein. In general, these terms will be used herein within their meaning in Euclidian space or in the Euclidian plane, but may be represented in other spaces by mathematical transformation. Thus, The term "space" herein encompasses any spaces defined in topology, regardless of dimension. In this connection, the term "trivalent" refers equally to planar triangles and to trihedrons.

Other geometrical references made herein include "congruence," which refers to the identity (but for orientation in space) of a form with another form; "similarity," which refers to forms that are congruent but for scale, and "symmetry," which refers to a property that a geometric object possesses if at least one translation, rotation, reflection or inversion operation can be performed on it that recapitulates the undisturbed object. The latter term is not to be confused with "order." One can apply these tests of symmetry to disordered patterns as well as to ordered patterns. Objects for which all rotations are symmetric are "rotationally isotropic." Objects for which all translations are symmetric are "translationally isotropic." "Translational invariance," as used herein, refers to a condition that may be revealed in a test object (i.e., an object being inspected for the condition) by moving an identical copy of the test object on (or through) the test object along a vector (i.e., in a defined direction), and finding that a defined point (or point pattern) in the copied object is congruent with an infinite discrete set of points in the object. Note that this definition implies, at least with respect to the direction of the vector, an object of infinite size (i.e., having no "edge).

The term "structure," as used herein is not intended to be limited to the concept of an assembly of classically mechanical elements. Some "structures" herein (e.g., the first Brillouin zone, described infra) may be better represented and analyzed in "reciprocal space" than in real space. To distinguish topologically defined structures from assemblies of classically mechanical elements, the latter are referred to herein as "compositions," "articles," or "articles of manufacture" assembled using "material-elements" made of "materials" (e.g., silicon). A given composition may comprise one or more species of material; a "material-element" does not imply that each such element is of only one size, shape, constitution or function.

A "crystal" usually refers to a system of bonded atoms arranged in periodically repeating sub-systems ("cells"). The term may be used herein more broadly to refer, without limitation, to any assemblage of points, lines, planes, volumes or other elements arranged in a periodic manner Such elements may be geometrical abstractions ("points") or they may comprise actual physical material. Typically, in systems of two or more dimensions, the periodically arranged elements are disposed in relation to one another in the form of a latticework. Familiarly, the "points" comprising the latticework are occupied by atoms chemically bonded to one another at the vertices of the faces of the lattice and the electron "cloud" associated with each such atom accounts, collectively, for the interference with the passage of electromagnetic energy (e.g., X-rays) through the lattice. Such lattices may have two-, three- or n-dimensions, and may be treated as being infinite: that is, having indefinite boundaries that encompass an essentially infinite number of cells. A particularly useful primitive cell for analytical purposes is the so-called "Wigner-Seitz" cell, found by identifying, for a selected vertex point, the set (or "locus") of vertex points in the lattice that are closer to the selected point than to any of the other points in the lattice. These points are in the "neighborhood" or "point-neighborhood" of the selected point (triangles having a vertex at a selected point are in the selected point's "triangle neighborhood"). A plurality of such cells can be assembled without "gaps" in between, or "overlaps," (i.e., the cells are "tessellated") and the result maps the overall structure of the lattice. One can pass an electromagnetic field-wave (X-rays, for example) through a real crystal, such that the wave is diffracted by its interaction with the electron clouds in the crystal, finally to illuminate a screen at a distance beyond. One will observe on the screen a pattern of light and dark spots, lines and/or circles (i.e., a "diffraction pattern"). The pattern is not an image of the crystal but it is the reciprocal of such an image. It is the crystal lattice in "reciprocal space." From it, one can construct a primitive cell that captures (the reciprocal of) the lattice structure of the entire crystal. This primitive cell is called the "first Brillouin zone" (or, for practical purposes, simply the "Brillouin zone").

A "photonic crystal" affects the passage of photons (i.e., electromagnetic waves) in particular by virtue of interfaces that occur periodically between two or more materials comprising the crystal. Because the materials have different refractive indices, light passing from one material into the other at an interface between them slows down (or speeds up), which bends the path of the light. The ensemble of such interfaces in a photonic crystal behaves collectively as if distributed in a latticework of points that scatter light. Light of a certain wavelength (or, more precisely, within a certain range or "band" of wavelengths) entering such a crystal in a certain direction may or may not traverse the crystal depending upon how it is refracted. Because a light wave is an electromagnetic excitation that oscillates in a plane (see infra), its traversal also depends upon the orientation of the plane in which the wave is traveling.

Light is an electromagnetic wave of energy produced by oscillating charges or magnets. In a vacuum, the wave propagates at 300,000 kilometers per second along a straight line called the propagation direction. In a dielectric material, it travels at a speed reduced by a factor "n," known as the refractive index. In a dielectric heterostructure, light moves through a heterogeneous mixture of materials with different dielectric constants and, hence, different light speeds.

At any point along the light wave, the electric field oscillates along an axis perpendicular to the propagation direction and a magnetic field propagates along an axis perpendicular to the electric field axis and the propagation direction. Light is called linearly polarized if the electric field axis is oriented in the same direction all along the wave. The axis of electric field axis oscillation is called the polarization or polarization direction. In general, light waves propagating in a certain direction can be decomposed into a combination of two independent polarizations, conventionally chosen to be perpendicular to one another (and the propagating direction). Light coming from a source can be polarized, which means a majority of light waves traveling in the same direction will have the same axis of electric field oscillation. Alternatively, it may contain an equal mixture of light with both polarizations.

In two dimensional photonic materials (or three-dimensional photonic materials with azimuthal symmetry), the material is used in such a way that light propagates along the two-dimensions (or in the plane perpendicular to the azimuthal direction). The polarization direction, which must be perpendicular to the propagation direction, may be purely in the azimuthal direction; this is called TM or TM polarization or TM polarized light. Alternatively, the polarization direction may be in the two dimensional plane (and perpendicular to the propagation direction); this is called TE or TE polarized light. The light may also contain a mixture of TM and TE polarized light. The same nomenclature is used to refer to two independent polarizations in three-dimensional photonic materials without azimuthal symmetry.

To the extent electromagnetic waves (e.g., light waves) of energy passing through a composition of matter interact with dielectric elements distributed within the composition as "obstacles" to the free passage of the energy, only waves of certain frequencies, moving in certain directions, will in fact pass through. Others, due to reflection, refraction or diffractive interference, will not. For a given direction of light travel, the composition may permit one or more distinct ranges, or "bands," of frequencies to pass through while prohibiting electromagnetic energy in other states from completely traversing it. These prohibited ranges define "band gaps" in the composition. It is not intended that the terms "band" and "band gap" herein have reference solely to electromagnetic waves. Energy, be it electromagnetic, electronic, acoustic, or otherwise, can exist in a composition only in certain states (frequencies, polarizations, etc.). The energy may, without limitation, be photonic (affected by electrical insulators, i.e., dielectric "obstacles"), electronic (affected by electrons transiently associated with atomic nuclei in a material), acoustic (affected by the mass of constrained but elastically vibrating atoms or "phonons"), or even a surface wave on a body of water (affected by macroscopic objects in its path) (Jeong et al, *Applied Physics Letters* 85:1645-1647, 2004).

As alluded to above, photonic band gaps do not exclude all lightwaves, only those of certain wavelengths traveling in certain directions and in certain modes. A "complete band gap," as the term is used herein, is a band gap that prohibits the passage of both TE-mode polarized and TM-mode polarized light. Complete band gaps are not necessarily equally proficient at blocking light travel in each mode. For example, a given complete band gap may prohibit TB-polarized light robustly, and TM-polarized light weakly. The band gap, although complete, is not "optimized." In fact, the excluded range of frequencies for the TE-mode is generally substantially different from the excluded range of frequencies for the TM-mode, so the bandgap is complete only where the two ranges intersect, i.e., in the range where both polarizations are excluded. Preferred embodiments of the present invention permit the construction of optimal complete band gaps in heterostructures.

Energy is carried in an electromagnetic wave or oscillating "field" in one direction indefinitely at the speed of light (in a vacuum) until the wave encounters an object that reflects it, absorbs it, delays it (as in "refraction"), or distorts it (as in "diffraction"). Electromagnetic waves can also interact ("interfere") with one another, additively to increase amplitude, or subtractively to extinguish all amplitude.

The amount of electromagnetic energy that impinges on an object in any given period of time depends OD how many waves (counted by their "crests," for example) reach the object during that period ("frequency") and the height of the wave (the "amplitude'). Short wavelengths mean high frequency, which, for a given amplitude, means more energy. Thus, electromagnetic energy can be denominated as frequency or as the number of waves that pass through a given space at a given speed ("wavenumber"). It is to be noted that since waves have both speed (or magnitude) and direction, they are vectors, symbolized herein by the bolded letter k. The magnitude of k is |k|. The (angular) wavenumber (k) of an electromagnetic wave is inversely proportional to the wavelength and is equal to |k|.

A "point pattern," as the term is used herein, refers to a pattern of points that may be used to derive a map or "blueprint" on which one may fabricate articles that embody the invention. Such articles may be fabricated to manipulate the flow of energy carried by waves, including but not limited to light energy. For example, the flow of energy carried by acoustic waves can be manipulated in some embodiments of the invention. In some embodiments, the invention provides a map having a two dimensional point-pattern. In some embodiments, the invention provides a map having a three-dimensional point-pattern. Advantageously, the patterns or maps are accessible for use in a computer. In this form, the structures they represent may be unbounded (to the extent computers permit). In one embodiment, useful in designing desired fabrications, the point-pattern is two-dimensional and has definable within it a completely convex (typically circular) "sampling window" of radius R that may be varied in size. In one embodiment, the point-pattern is three-dimensional and has definable within it a completely convex (typically spherical) window. It is not intended that embodiments be limited to two or three dimensions. One-dimensional and n-dimensional point-patterns are also contemplated.

The "structure factor" of a structure relates to the "order" that the points of interest collectively assume in a structure under one or another condition, in the sense that the structure factor is a measure of the probability that the structure will scatter a wave of wavenumber k, which probability, in turn, is affected by the arrangement of the scatter-points in the structure. A structure factor may also be referred to as a "structure function," "power spectrum," "power density spectrum" or "S(k)". The "order" of a point-pattern in a structure relates herein to a property exhibited by a population of points arranged or distributed in an array along a line, or in n-dimensional space. That property may be measured in terms of "number variance." In any sampling window in which one inspects a region of the structure, one will find a certain point-density (e.g., points/unit volume). By moving the inspection window repeatedly without changing its size (i.e., its volume in a three-dimensional structure), and counting the number of points encountered in the window each time the window is moved, one may readily determine the average number of points observed and the variance in the number observed for that window size. As one changes the size (surface or volume) of the window, the number variance in the observed point-density will vary in a way that depends upon how the points in the population are ordered. If the points are distributed randomly in the structure (i.e., according to Poisson statistics), the increase in the volume of the observation window and the increase in number variance will be equal. If distributed hyperuniformly, the increase in number variance will grow only as a fraction of the increase in the volume.

In physical systems, structure functions and power spectra provide information about how points of mass, charge, energy, etc. distribute themselves in the system. A crystal is an example of a physical system comprising points that scatter impinging radiation ("scatter-points"). The radiation that scatters from the crystal depends on the crystal's structure function which, in turn, depends on the extent to which—and the manner in which—the density of scatter-points fluctuates through the crystal.

To rationalize the concept of "order" in point-patterns, at least three types of "order" are referred to herein. "Random order" refers to structures having point-patterns such that the statistics of point-density fluctuations in any (normalized) sample of the structure (e.g., the sample variance) are consistent with a random (or "Poisson") distribution. Stated quantitatively, the number variance of a purely random point-pattern in two dimensions or three dimensions varies exactly as the area (d=2) or the volume (d=3) of the window varies. "Homogeneous" or "uniform" order refers to structures whose point-density fluctuations are statistically the same from sample-to-sample. Stated in another way, the variance of any statistically homogeneous, isotropic point pattern grows more slowly than the window's volume grows, but cannot grow more slowly than the window's surface grows. The number variance of a hyperuniform point pattern grows more slowly than the window's volume—by a fraction that is strictly less than one.

However, the number variance of a major subclass of homogeneous, isotropic point patterns grows exactly as the surface grows. This subclass is also referred to herein as "hyperuniform" or "superhomogeneous." This one subclass of hyperuniform patterns is called "stealthy" because, for a certain set of wavelengths (that is, where the wavenumber ranges from k=0 to k=+$k_e$), a light-scattering structure built according to such a point-pattern will not scatter light: for that set of wavelengths, the structure factor is exactly zero ($S_k$=0). Quantitatively, $\langle N_R^2 \rangle - \langle N_R \rangle^2 = AR^p$, where the brackets refer to averages over many independent sampling windows of radius R. The relation determines the number variance in an average window of radius R ($N_R$ being the number of points lying within the window), where p≥d−1 and p<d. This means that the number variance must grow more slowly than the volume of the window in three dimensions (that is, 2<p<3), or more slowly than the surface area of the window in two dimensions (1<p<2). For example, it is common for p to be equal to 2 or 1 in three or two dimensions, respectively. The test for hyperuniformity in point-patterns is provided in greater detail by Torquato et al. in *Phys. Rev. E* 68: 41113, 2003. The proportionality constant A for the relation above determines the degree of hyperuniformity, smaller values reflecting greater hyperuniformity.

Described below is an "inverse" use of the "collective coordinates" method (Uche et al., *Phys. Rev. E* 74:031104, 2006) to design point patterns from whatever scattering characteristics may be desired for a particular structure. Collective coordinates are derived from measurements of the co-ordinates or locations (plotted as wavevectors) of particles in their density field. In the inverse, the wavevectors associated with the desired scatter are employed to locate the appropriate scatter-points for the structure. Essentially, the exercise amounts to constraining some coordinates (i.e., reducing degrees of freedom) and not others. The system quantity χ is the ratio of the number of constrained degrees of freedom to the total number of degrees of freedom in the system. Essentially, it equals the fraction of wavenumbers k within the Brillouin zone that are set to zero The peculiar tendency of "stealthy" hyperuniform structures to show no long range order persists as χ increases until χ reaches a dimension-dependent critical value χc, beyond which the pattern attains long-range translational order. For two-dimensional systems, χc~0.77.

DETAILED DESCRIPTION

In one aspect, embodiments of the invention provide methods of designing structures of use in emitting, transmitting, amplifying, detecting and modulating energy or energy quanta. The methods apply in particular to designing structures that emit, transmit, amplify, detect or modulate quanta of light (i.e., photons) or the equivalent thereof in the form of electromagnetic waves. The methods are applicable especially to structures that can be assembled without the degree of precision required by structures that rely on periodicity (e.g., crystals) to impart their effects on photons or, more pertinently in the present context, electromagnetic waves.

Structures that affect the passage of light therethrough generally comprise elements that scatter light. These elements form a variety of geometric patterns that can be represented diagrammatically as collections of points or "scatter-points." Light that passes through a given collection of scatter-points, whether it arises from outside the structure or from within the structure, forms a diffraction pattern when it emerges. The diffraction pattern is a function of the geometric scatter-point pattern, as illustrated in FIG. 1. One can see by inspection that the point pattern shown in panel A is disordered. Inspection of the point pattern in panel B also exhibits disorder, but the impression of "clustering" is less prominent. Neighboring points may be quite close to one another but, over the entire field of view, highly dense clusters are not discernible. The sense of randomness is muted. More formally stated, fluctuations in density grow with the circumference or radius rather than area. This is a hallmark of homogeneity (uniformity).

Figure 6:
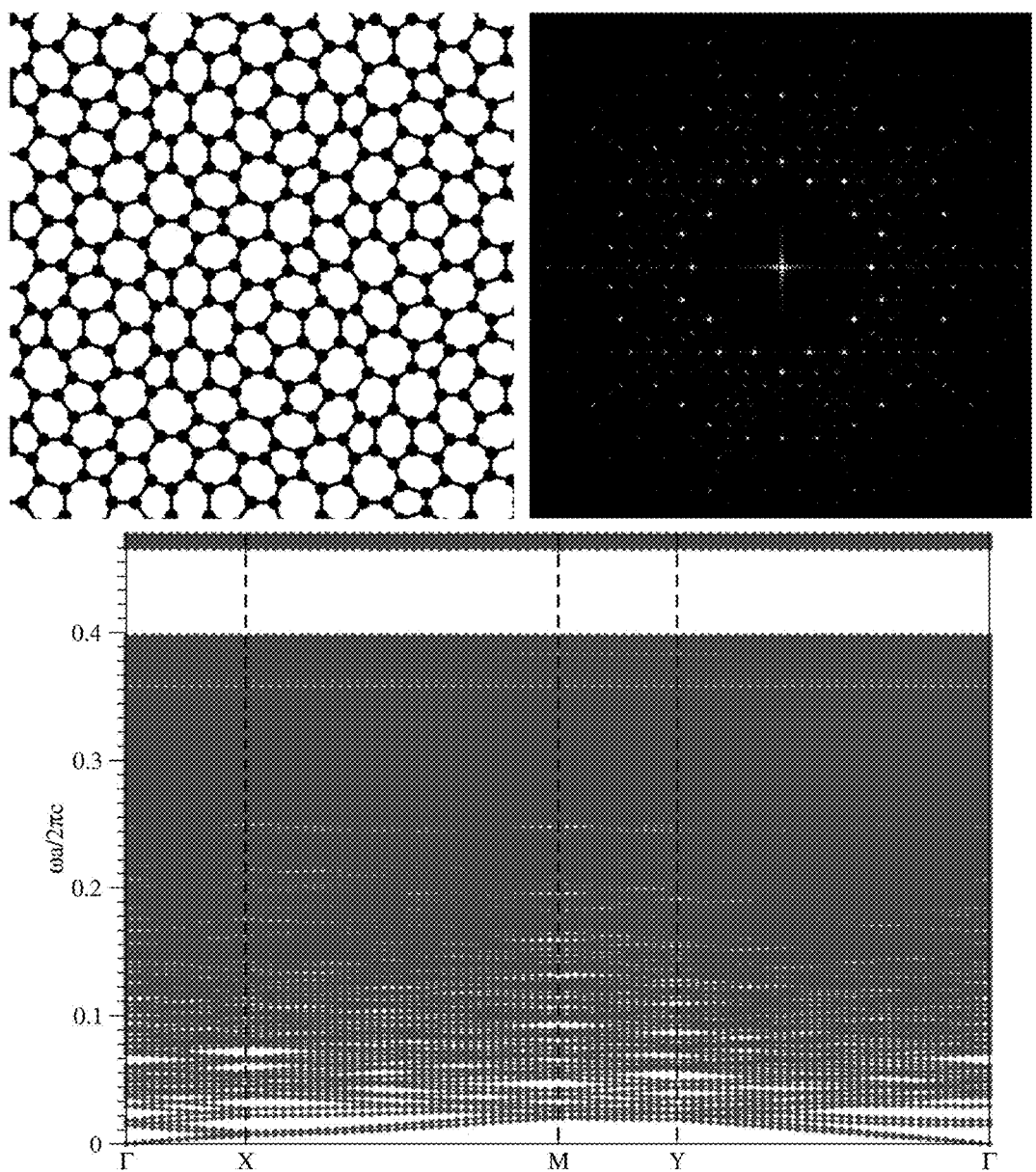
FIG. 6 shows a representation (tessellation, diffraction pattern and band gap structure) of a hyperuniform structure having sufficient translational periodicity to confer on it the five-fold symmetry of a quasicrystal.

Many hyperuniform structures show translational periodicity. Hyperuniform patterns can be translationally disordered or ordered, and isotropic or anisotropic. Regular (periodic) crystals, which are anisotropic and translationally disordered, are hyperuniform by the criterion defined above. Generally, quasicrystals also qualify. Although quasicrystals are aperiodic in the sense that they lack periodic translational symmetry in real space, their diffraction patterns (i.e., their reciprocal lattices) are consistent with periodicity. The diffraction patterns consist of Bragg peaks, and their number variance and S(k) are consistent with the definition of hyperuniformity. An example of a quasiperiodic crystal having five-fold symmetry and a hyperuniform structure is provided in panel C of FIG. 1 and in FIG. 6. Point-patterns that conform to a Poisson (i.e., random) distribution are not periodic and are not hyperuniform. However, some disordered (and non-periodic) point patterns, reflected in certain embodiments of the present invention, are hyperuniform.

A prime objective in designing photonic crystals is to build into them complete photonic band gaps. The ability to manipulate the flow of light depends on such band gaps. It has generally been thought that the periodic nature of crystals is a determinant of their ability to accommodate complete photonic band gaps. Surprisingly, the applicants have found, in simulations, that complete band gaps can be incorporated into some non-crystalline (i.e., non-periodic) materials, including disordered materials. Therefore, in another aspect, embodiments of the invention provide articles comprising arrangements of structural elements that need not confer periodicity on the composition to provide complete photonic band gaps in the composition. In fact, embodiments of the invention include any article of manufacture that relies on a complete photonic, phononic or electronic band gap for functionality, and is non-crystalline (i.e., non-periodic) but is "disordered/hyperuniform." To make any such article, one proceeds according to the guidance that the prior art provides for making the periodic version of the article, but simply substitutes a disordered/hyperuniform non-crystalline pattern. By way of non-limiting example, U.S. Pat. No. 6,869,330 to Gee et al. discloses a method for fabricating a photonic crystal from tungsten for use in an incandescent lamp having improved efficiency. A mold is fashioned lithographically in a silicon substrate according to a pattern dictated by a photolithographic etch mask. The pattern in the mask is characterized by a periodicity but, according to the instant invention, may be characterized by the disordered/hyperuniform criterion instead, thereby producing a non-crystalline incandescent emitter having improved efficiency compared to conventional tungsten filaments. U.S. Pat. No. 6,468,823 to Scherer et al. discloses a method by which devices that comprise photonic crystals (such as waveguides, microcavities, filters, resonators, lasers, switches, and modulators) can be made using a two-dimensional photonic crystal structure. The structure is based on patterning by means of mask lithography. Again, by laying out the patterning such that the disordered/hyperuniform condition is achieved, the present invention may be embodied in waveguides, microcavities, filters, resonators, lasers, switches, modulators, etc. Three-dimensional photonic crystals can also be fabricated by lithography. U.S. Pat. No. 7,588,882 to Romanato et al. is exemplary. Again, the present invention may be embodied in devices such as those noted in Romanato et al. by substituting a disordered/hyperuniform non-crystalline pattern for the conventional crystalline pattern. Disordered/hyperuniform non-crystalline versions of selective band-pass filters and photovoltaic solar cells are also within the scope of the invention and can be made for the X-ray, ultraviolet, visible, infrared and microwave electromagnetic radiation regimes using, for example, the layer growth techniques set forth in U.S. Pat. No. 6,064,511 to Fortmann et al. In this case, hydrogen radical beams are directed onto a substrate through a plurality of collimators laid out in a desired pattern, which pattern may be disordered/hyperuniform.

The acoustic regime is also susceptible to manipulation in disordered/hyperuniform structures having a phononic band gap. U.S. patent Application 2009/0295505 to Mohammadi et al., describes a method of making a so-called "phononic crystal" that prohibits passage therethrough of wave-mechanical energy of certain wavelengths. One can use the same method to make disordered/hyperuniform non-crystalline phononic devices that filter, confine or guide mechanical energy and hence are useful for a variety of applications including wireless communications and sensing. It is necessary only to substitute the disordered/hyperuniform pattern for the crystalline pattern used by Mohammadi et al.

The selective transmission of electrons through crystalline materials (such as silicon) having electronic band gaps is the basis of semiconduction and countless devices based thereon. Electronic band gaps can also be fabricated in amorphous (non-crystalline) silicon, advantageously by implantating self-ions into crystalline silicon (Laaziri et al. Physical Review Letters 1999, 82:3460-3463). Thus, if one employs this method in combination with methods that are in accord with the instant invention, the electronic regime may also be subject to manipulation in disordered/hyperuniform structures.

Finally, another non-limiting method of fabricating a hetero structure according to embodiments of the invention is described in U.S. Patent Application Publication No. 2009/0212265 to Grier et al.

The patents and patent applications, cited above by way of example and not of limitation, are incorporated herein in their entirety for all purposes.

Although it is not necessary for patentability to understand how an invention, in any embodiment, works, the applicants believe that hyperuniformity may play a role. In any case, non-periodic structures having complete band gaps built into them constitute a new class of materials, some of which may be at least as useful as many periodic structures: the band gaps of the non-periodic (i.e., translationally disordered) structures can be sizeable; their accessibility is not subject to rotational symmetry limitations (they are rotationally isotropic); and constraints on the placement of defects to control the flow of light are relaxed. Limitations that the symmetry planes in periodic photonic crystals impose on waveguide fabrication are reduced or removed. Attainable band gap sizes ($\Delta\omega/\omega_c$) are more than about 5%, preferably more than about 10%, and more preferably more than about 20% (where $\Delta\omega$ is the "width" of the band gap, i.e., the range of prohibited wave frequencies, and $\omega_c$ is the midpoint of that range). In a preferred embodiment, the invention provides a heterostructure having high dielectric contrast. In one embodiment, the heterostructure comprises silicon and air. Non-limiting alternatives to silicon include alumina, tungsten, etc. The recognition that hyperuniform structures have these advantages will motivate efforts to improve the degree of hyperuniformity in such structures, which in turn will penult persons of skill in the art to use embodiments of the invention for many purposes.

To make a disordered heterostructure with a complete band gap according to a preferred embodiment of the invention, one may first lay out (i.e., "construct") a translationally disordered hyperuniform point pattern. The "collective coordinate" protocol from Batten et al. (2008) enables one to create a large class of tailored hyperuniform point patterns by using a large class of targeted functional forms for the structure factor S(k). Given a target structure factor S(k) corresponding to a desired hyperuniform point pattern, the algorithm starts with an initial arbitrary configuration of points within a simulation box. Successive configurations of points are then sequentially moved according to an optimization technique that in the final steps results in the targeted structure factor. An example of a class of hyperuniform point patterns that can be used to make disordered heterostructures are "stealth" point patterns. Such patterns have a structure factor S(k) that is precisely equal to zero for all $|k|<k_c$ for a selected (positive) value of the critical wavenumber $k_c$ and tends to unity for large k values. Such structures are referred to as "stealthy" because they completely suppress scattering for $|k|<k_c$. The structure is therefore invisible at wavelengths that meet this criterion. Provided that $k_c$ is above some threshold value, the disordered heterostructure derived from these stealthy patterns will have a complete band gap. By tuning $k_c$, one can increase the size of the band gap to sizes comparable to some photonic crystals.

In further detail, the method utilizes an inverse approach: one prescribes scattering characteristics (e.g., absolute transparency) and constructs many-body configurations that give rise to these targeted characteristics. One first applies the methodology initially for structureless (i.e., point) particles and then generalizes to structured particles, colloids, etc.

It is to be noted that systematically increasing the system size has no effect on the degree of disorder. Constructed configurations remain disordered in the infinite-volume limit (i.e., where inter-particle distances are much less than the size of the system).

"Stealth" materials refer to many-particle configurations that completely suppress scattering of incident radiation for a set of wave vectors, and thus, are transparent at these wavelengths. Periodic (i.e., crystalline) configurations are, by definition, "stealthy" since they suppress scattering for all wavelengths except those associated with Bragg scattering. The method discussed here, however, constructs disordered stealth configurations that prevent scattering only at prescribed wavelengths with no restrictions on any other wavelengths.

To characterize the local order of an ensemble, one uses pair information in real space via the pair correlation function $g_2(r)$ and in reciprocal space through the structure factor S(k) as these functions are experimentally accessible and used widely in many-body theories.

The pair correlation function is the normalized two-particle probability density function $\rho_2(r)$ and is proportional to the probability of observing a particle center at r relative to a particle at the origin. For a statistically homogeneous and isotropic medium, the pair correlation function depends only on the magnitude of r≡|r|, and is commonly referred to as the radial distribution function $g_2(r)$.

The structure factor is proportional to the intensity of scattering of incident radiation from a configuration of N particles and is defined as $$S(k) = \frac{\rho(k)}{N} \tag{M1}$$

where $\rho(k)$ are the collective coordinates and k are the wave vectors associated with the system volume and boundary conditions. Collective coordinates are the Fourier coefficients in the expansion of the density field:

$$\rho(k) = \sum_{i}^{N} e^{ik \cdot r_j} \tag{M2}$$

where $r_j$ denotes the location of particle j. When S(k) depends only on the magnitude of k≡|k|, the structure factor S(k) is related to the Fourier transformation of $g_2(r)-1$, ignoring the forward scattering associated with k=0, $$S(k)=1+\int e^{ik \cdot r_j}[g_2(r)-1]dr \tag{M3}$$

where ρ is the number density. For highly ordered systems, both $g_2(r)$ and S(k) contain a series of δ-functions or peaks at large r and k, indicating strong correlations at the associated pair distance. In configurations without long-range order, both $g_2(r)$ and S(k) approach unity at large r and k.

The method has the advantage of targeting pair information in reciprocal space to construct configurations whose structure factor exactly matches the candidate structure factor for a set of wavelengths. In addition, the procedure guarantees that the resulting configuration is a ground-state structure for a class of potential functions.

The numerical optimization procedure follows that of Uche, Stillinger and Torquato, Phys. Rev. E 74, 031104 (2006) used to tailor the small k behavior of the structure factor. The structure factor S(k) and collective coordinates ρ(k), defined in Eqs. M1 and M2, are related to the quantity C(k), $$S(k) = 1 + \frac{2}{N}C(k) \tag{M4}$$

where $$C(k) = \sum_{j=1}^{N-1}\sum_{i=j+1}^{N}\cos[k \cdot (r_j - r_i)]. \tag{M5}$$

For a system interacting via a pair potential $v(r_i-r_j)$, the total potential energy can be written in terms of $C(k)$, $$\Psi = \sum_i \sum_j v(r_i - r_j) = \Omega^{-1} \sum_k V(k)C(k) \qquad (M6)$$

where $\Omega$ and $V(k)$ is the Fourier transform of the pair potential function $$V(k) = \int_\Omega dr\, v(r) e^{ik \cdot r} \qquad (M7)$$

For a region of space with dimensions $L_x$; $L_x \times L_y$, or $L_x \times L_y \times L_z$ in one, two, or three dimensions, subject to periodic boundary conditions, the infinite set of corresponding wave vectors has components $$k_\gamma = \frac{2\pi n_\gamma}{L_\gamma} \qquad (M8)$$

where $n_\gamma$ are positive or negative integers, or zero and $\gamma = x,y,z$ as needed. For example, in three dimensions, the set of wave vectors are $$k = \left( \frac{2\pi n_x}{L_\gamma}, \frac{2\pi n_y}{L_\gamma}, \frac{2\pi n_z}{L_\gamma} \right) \qquad (M9)$$

It is clear that for any positive $V(k)$ for $|k|<K$ but zero otherwise, the global minimum of the total potential energy in M6 is achieved by driving $C(k)$ or $S(k)$ to its minimum value for all $|k|$ (Uche et al., Phys. Rev. E 74: 31104, 2006).

For simplicity, one may utilize a "square mound" $V(k)$, i.e., a function that is a positive constant $V_0$ for all $k \in Q$, where Q is the set of wave vectors such that $0<|k|<K$, and zero for all other k. In the infinite-volume limit, this corresponds to a system of particles interacting via a real-space pair potential function that is bounded, damped, and oscillating about zero at large r. (Fan et al., Phys. Rev. A 44: 2394, 1991; Uche et al., Phys. Rev. E 70: 46122, 2004; Uche et al., Phys. Rev. E 74: 31104, 2006). This choice of pair potential serves our immediate purposes to generate many-particle configurations with tuned scattering characteristics as a numerical tool only. Such soft potentials are of physical importance in soft-matter physics and are easier to treat theoretically (Torquato and Stillinger, Phy. Rev. Lett. 100: 20602, 2008). The specific form of $V(k)$ is largely irrelevant in the design of scattering patterns so long as it is positive, bounded, and has compact support up to $|k|=K$. To approximate physical systems, $V(k)$ may be chosen so that there is strong repulsion in $v(r)$, for small r. For a cutoff radius K, there are $2M(K)$ wave vectors in the set Q where $M(K)$ is the number of independently constrained collective coordinates. That is, constraining $C(k)$ implicitly constrains $C(-k)$ due to the relation:

$$C(k) = C(-k).$$

For a system of N particles in d dimensions, there are Nd total degrees of freedom. We introduce the dimensionless parameter $\chi$ to conveniently represent the ratio of the number of constrained degrees of freedom relative to the total number of degrees of freedom $$\chi = \frac{M(K)}{Nd}. \qquad (M10)$$

The global minimum of the potential energy defined in Eq. M6 has the value of $$\min_{r_1 \ldots r_N}(\Psi) = -\frac{N}{2} \sum_{k \in Q} V_0$$

if and only if there exist particle configurations that satisfy all of the imposed constraints, which necessarily occurs for $\chi < 1$. Minimizing Eq. M6 to its global minimum, for $\chi < 1$, yields ground-state configurations that are stealthy for all $k \in Q$.

To target a specific form of the structure factor to certain nonzero values, such as $S(k)=1$, we introduce a second nonnegative objective function, $$\Psi = \sum_{k \in Q} V(k)[C(k) - C_0(k)]^2 \qquad (M11)$$

where $C_0(k)$ is associated with the target structure factor by Eq. M4. If Eq. M11 is taken to be the potential energy of an N-body system, then two-, three-, and four-body interactions are present (Uche et al., Phys. Rev. E 74: 31104, 2006). Equation M11 has a global minimum of zero, for $\chi<1$, if and only if there exist configurations that satisfy all of the imposed constraints. Minimizing Eq. M11 is used to construct super-ideal gases and equi-luminous materials as ground-state configurations.

Three algorithms have been employed previously for minimizing Eqs. M6 and M11: steepest descent (Fan et al., Phys. Rev. A 44: 2394, 1991), conjugate gradient (Uche et al., Phys. Rev. E 70: 46122, 2004), and MINOP (Uche et al., Phys. Rev. E 74: 31104, 2006). Steepest descent and conjugate gradient methods are line search methods that differ only in their choice of search directions (Press, Numerical Recipes in C: The Art of Scientific Computing, Cambridge Univ. Press, 1992). The MINOP algorithm is a trust-region method. When far from the solution, the program chooses a gradient direction, but when close to the solution, it chooses a quasi-Newton direction (Dennis and Mei, J. Optim. Theory Appl. 28: 453, 1979; Kaufman, SIAM J. Optim. 10: 56, 1999). Upon each iteration, the program makes an appropriate update to approximate the Hessian (Kaufman, SIAM J. Optim. 10: 56, 1999).

Neither the conjugate gradient method nor MINOP algorithm significantly biases any subset of ground-state configurations. The resulting configurations are visually similar, and the ensemble-averaged radial distribution function and structure factor produced by both methods have similar features. The MINOP algorithm may be advantageous because it has been demonstrated to be better suited to the collective coordinate procedure than the conjugate gradient method (Uche et al., Phys. Rev. E 74: 31104, 2006).

Three sets of initial conditions were considered: random placement of particles (Poisson distributions), random sequential addition (RSA), and perturbed lattices (integer, triangular, and face centered cubic in one, two, and three dimensions respectively). For an RSA process, particles are assigned a diameter and randomly and irreversibly placed in space such that particles are not overlapping (Torquato, Random Heterogeneous Materials: Microstructure and Macroscopic Properties, Springer Verlag, N.Y., 2002). At sufficiently high $\chi$, usually $\chi > 0.6$, the constructed ground-state systems apparently lose all memory of their initial configurations. The analyses presented in the following sections will be those of random initial conditions. In some cases at large $\chi<1$, a global minimum is not found. For the results discussed here, Eqs. M6 and M11 were minimized to within $10^{-17}$ of their respective minimum value. All other trials were excluded from the analysis.

The region of space occupied by the N particles was limited to a line in one dimension, a square in two dimensions, and a cube in three dimensions, with periodic boundary conditions. For stealth materials, particular attention was paid to the choice of N for two and three dimensions. Minimizing Eq. M6 for large $\chi<1$ is known to yield crystalline ground states (Fan et al., Phys. Rev. A 44: 2394, 1991; Uche et al., Phys. Rev. E 70: 46122, 2004; Uche et al., Phys. Rev. E 74: 31104, 2006). We choose to be consistent with previous studies. In two dimensions, N was chosen as a product of the integers 2pq, and p/q is a rational approximation to $3^{1/2}$ so that all particles could be placed in a triangular lattice configuration without substantial deformation. In three dimensions, N was usually chosen so that $N=4s^3$, where s is an integer, so that the particles could be placed in a face centered cubic lattice without deformation. In minimizing Eq. M11, N occasionally was assigned other values.

Designing the Band Gap.

Figure 2:
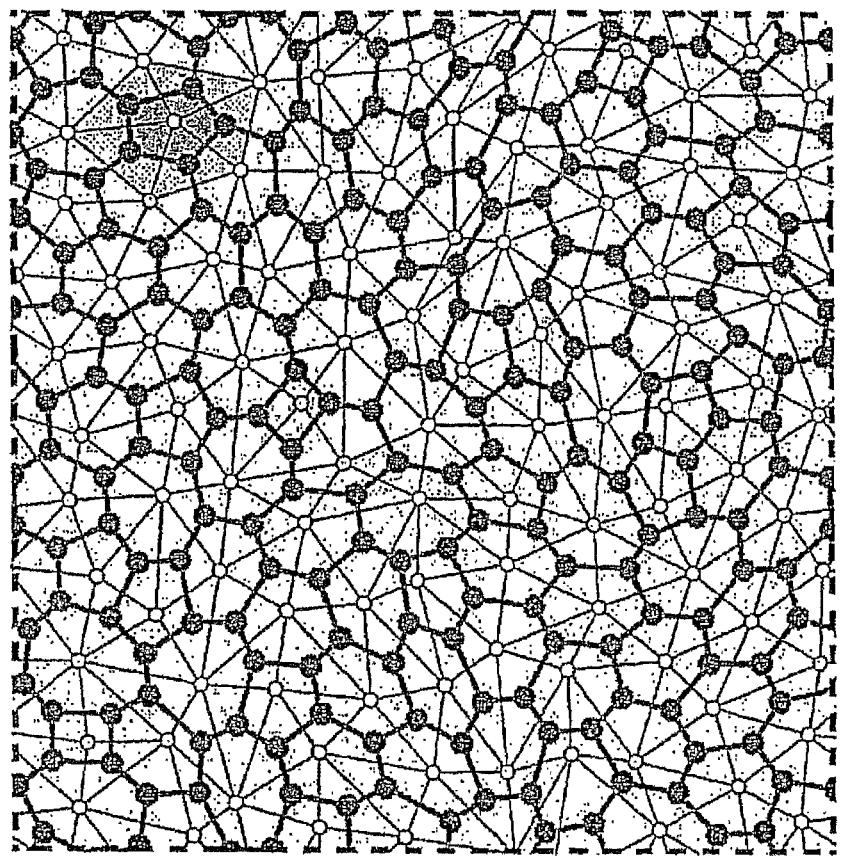
FIG. 2 shows a map in two dimensions of a photonic structure built up from a hyperuniform point-pattern.

A photonic band gap structure may be computed for "stealthy" structures, including but not limited to non-crystalline structures, as follows:

After selecting and plotting a point pattern with the desired rotational symmetry and translational order, the next step is to determine the arrangement of dielectric materials around the selected point pattern that will produce the largest complete band gap. The applicants present herein a novel method for transforming the selected point pattern, whether crystal, quasicrystal or disordered hyperuniform, into a tessellation of cells with the selected translational and rotational symmetry but having a nearly optimal photonic band gap structure (with band gaps within a percent or less of absolute optimal). Because the procedure requires varying over only two degrees of freedom, the protocol uses much less computational resources than other methods. In one embodiment, the invention provides a method, beginning from the disordered hyperuniform point pattern of open circles shown in FIG. 2, as discussed below.

If the goal were simply to have a band gap that only blocks TM polarization (electric field oscillating along the azimuthal direction, that is, perpendicular to the plane of propagation and at the same time perpendicular to the to the TE plane), it would suffice to replace each point with a circular cylinder and vary the radius of the cylinders until the structure exhibits a maximum TM band gap. However, this design is poor for blocking TE polarization (electric field oriented in the plane). To obtain a design that optimally blocks TE modes well, one may construct a Delaunay tiling from the original two-dimensional point pattern, find the centroid of each tile (alternatives to centroids are also possible, and connect the centroids that surround each point to transform the centroid point-pattern into a tessellation of cells. One may then decorate the cell edges with walls (along the azimuthal direction) of dielectric material of uniform width w and vary the width of the walls until the maximal TE band gap is obtained. Finally, to obtain designs exhibiting overlapping TM and TE gaps, one may construct an optimal compromise structure by adding one other step: the vertices of the trihedral network of cell walls may be decorated with circular cylinders (black circles in FIG. 2) of radius r. For a given set of dielectric materials, the optimal complete band gap may be achieved by varying the only two free parameters, the cell wall thickness w and the circular cylinder radius r. Moreover, the optimized band gap is equivalent to the fundamental band gap in periodic systems, $n_B=N$, where $n_B$ is the band gap number and N is the number of points per unit cell.

Figure 4:
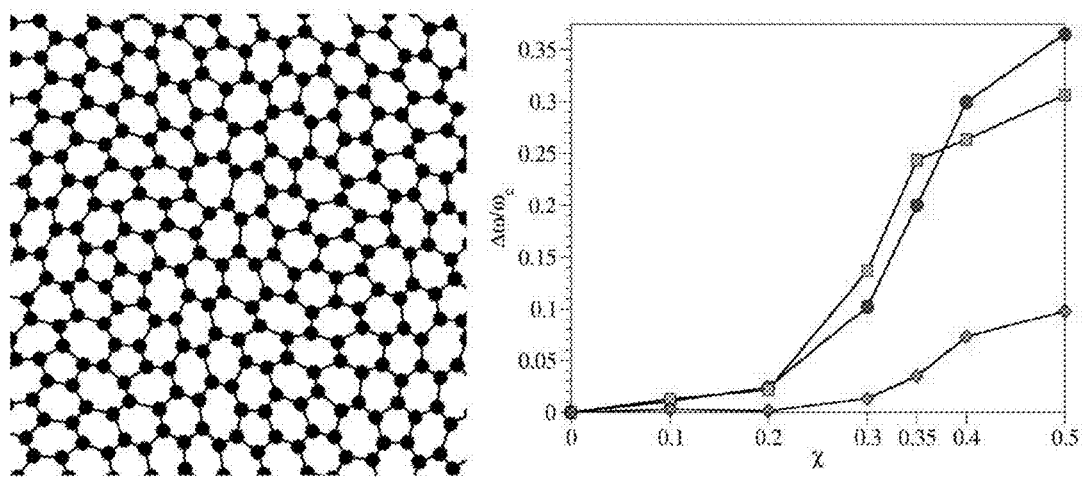
FIG. 4 shows a map in two dimensions of a disordered hyperuniform photonic structure optimized for a complete band gap (left panel) and a graph showing how the TM, TE and complete band gaps behave as a function of $\chi$.

Previous attempts to create band gaps in photonic quasicrystals and disordered systems have been reported that produce either TM band gaps or TE band gaps, but not both. The focus has been in finding the widest possible TM or TE band gap, but, as it turns out, the optimal design for one is a poor design for the other and vice versa. By contrast, the procedure described above, based on hyperuniformity, leads to an optimal compromise aimed at finding the widest band gap for both polarizations. The disordered/hyperuniform photonic structure shown in FIG. 4 is exemplary. Complete band gaps (diamonds) open up at $\chi>0.3$, at which point both TE (circles) and TM (squares) band gaps are sizeable.

Figure 3:
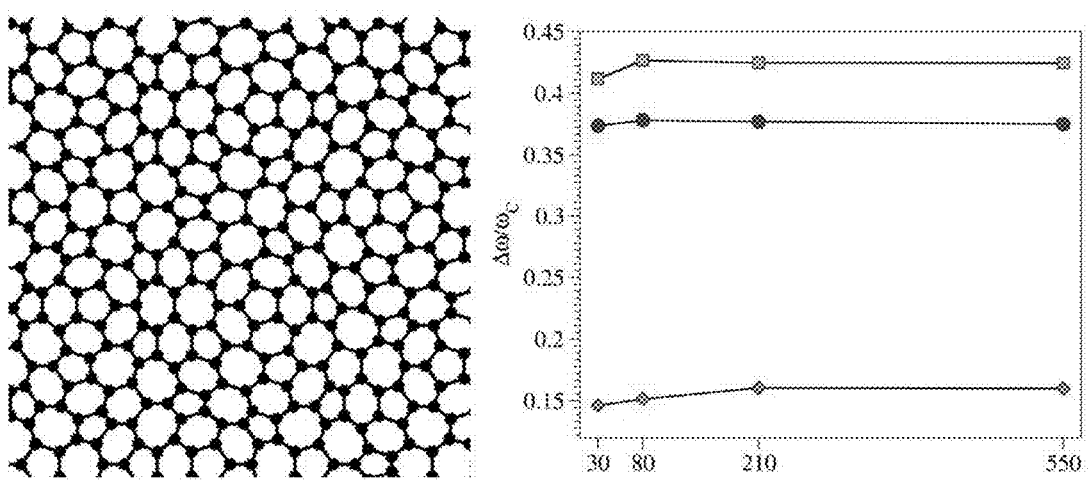
FIG. 3 shows a map in two dimensions of a quasicrystalline photonic structure with five-fold symmetry (left panel) and the fractional band gaps ($\Delta\omega/\omega_c$) therein (as a function of the number of scattering elements) for TM-blocking (circles), TE-blocking (squares) and complete blocking.
Figure 7:
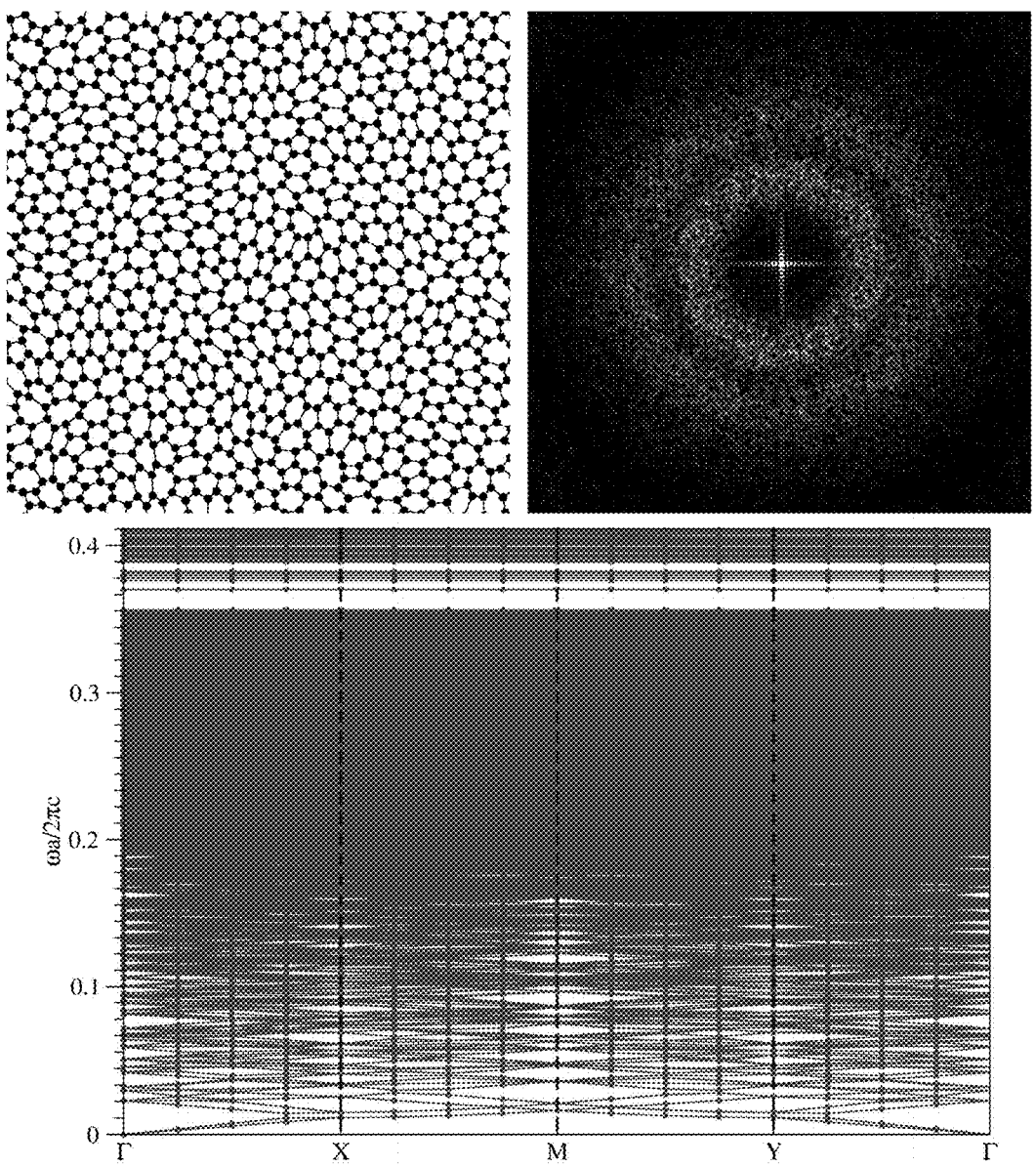
FIG. 7 shows a representation (tessellation, diffraction pattern and band gap structure) of a disordered hyperuniform structure optimized for $\chi=0.35$.
Figure 8:
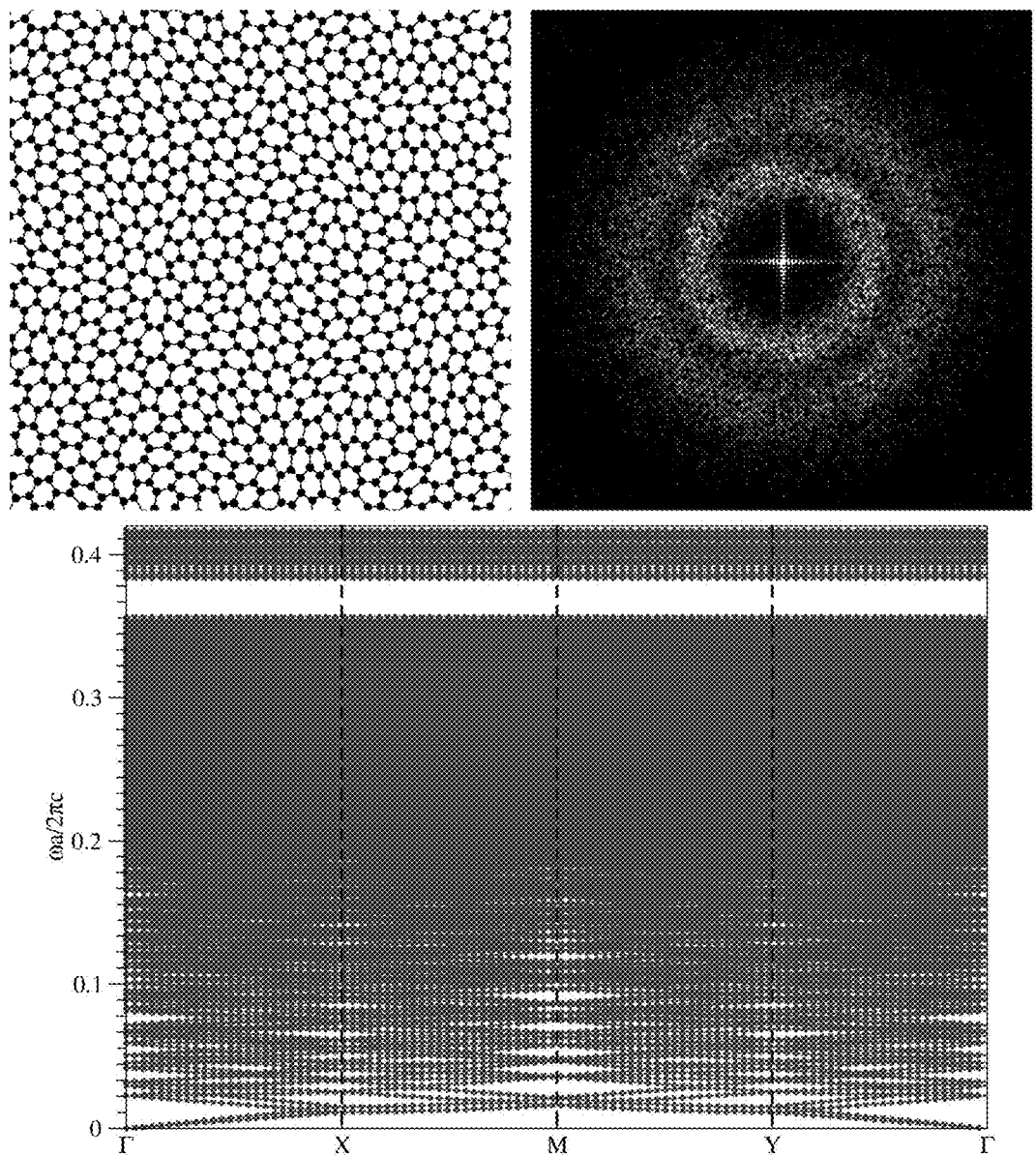
FIG. 8 shows a representation (tessellation, diffraction pattern and band gap structure) of a disordered hyperuniform structure optimized for $\chi=0.4$.

To illustrate one embodiment (but not intending any limitation), one may assume the photonic materials are composed of silicon (with dielectric constant $\varepsilon=11.56$) and air. For disordered photonic structures, one may construct a sequence of periodic approximants (i.e., disordered structures treated in the same way a perfectly periodic structure would be treated) with a "stealthy" disordered arrangement of points as discussed above within a square array of length L in which the number of points per unit cell N ranges from about 100 to about 500 (see the horizontal axis of the graph on the right-hand side of FIG. 3). For fixed $\chi$, the simulated gap width remains essentially constant as N varies between 100 and 500 (FIG. 3). One may conveniently use a length scale $a=L/\sqrt{n}$, such that all patterns have the same point density $1/a^2$. A significant band gap begins to open for sufficiently large $\chi \sim 0.35$ (but well below $\chi_c$), at a value where there emerges a finite exclusion zone between neighbouring points in the real space hyperuniform pattern (FIGS. 4 and 7). In reciprocal space, this value of $\chi$ corresponds to the emergence of a range of "forbidden" scattering, $S(k)=0$ for $k<k_c$ for some positive $k_c$, surrounded by a circular shell just beyond $k=k_c$ with increased scattering. The structures built around hyperuniform patterns with $\chi=0.5$ are found to exhibit remarkably large TM (of 36.5%) and TE (of 29.6%) photonic band gaps making them competitive with many of their periodic and quasiperiodic counterparts. More importantly, there are complete photonic band gaps of appreciable magnitude reaching values of about 10% for $\chi=0.5$, independent of any finite L. FIG. 8 shows the optimal photonic band gaps for the case $\chi=0.4$, FIG. 9 for the case $\chi=0.5$.

Figure 5:
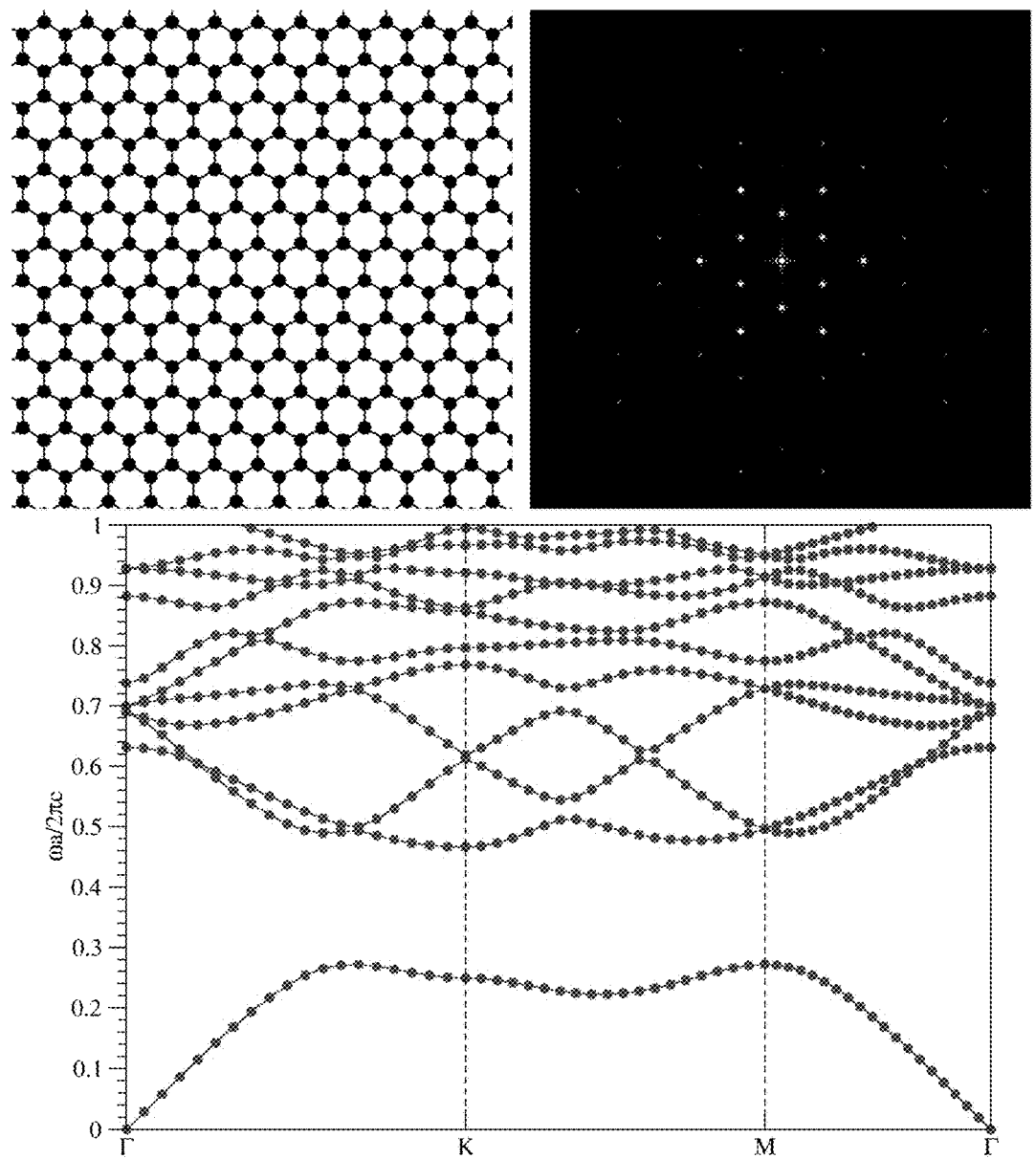
FIG. 5 shows a prior art representation of an optimal photonic crystal. Upper left panel shows a tessellation in two dimensions of the cells of the crystal; upper right panel shows its diffraction pattern and the graph depicts the structure of the crystal in terms of its band gaps.
Figure 9:
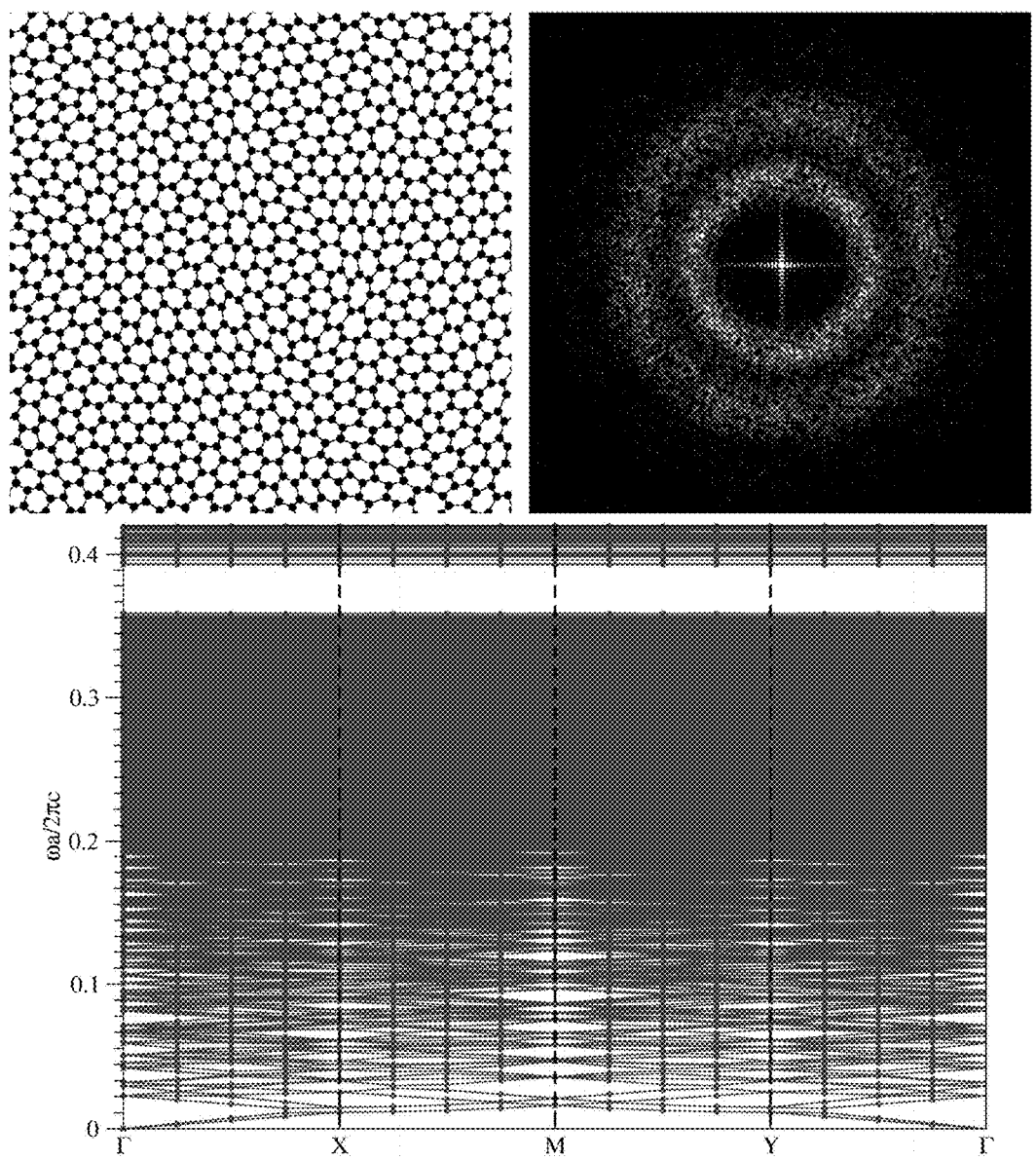
FIG. 9 shows a representation (tessellation, diffraction pattern and band gap structure) of a disordered hyperuniform structure optimized for $\chi=0.5$.

For comparison, FIG. 5 shows the "layout" of an optimal photonic crystal structure (a), its simulated diffraction pattern (b), and its simulated photonic band gap structure (c). The band gap structure plot represents how the energy (or frequency) of a photonic state ($\omega$) varies with incident angle (the x-axis). Instead of showing angle explicitly, the convention of indicating how close the incident angle is to one symmetry axis or another is followed; the symmetry axes are labelled Γ, K, M, and then another Γ symmetry axis. For a square lattice, for example, this would show how the energy varies depending on how close the incident angle comes to hitting an edge or corner directly. The bottom curve shows, for example, that the energy varies substantially. Note that, above the 0.5 level on the y-axis, the curves "crisscross" so that one cannot draw a line from left to right without hitting a line. This means "NO BAND GAP." That is, light impinging with this energy, at some angle of incidence, will pass through the lattice. On the other hand, note that a range exists between the bottom curve and the next ones above it that will accept lines drawn left to right. At some angles of incidence, the gap is wide, at others narrower. That is, the crystal structure is "anisotropic." The quasicrystalline structure of FIG. 6 and the disordered hyperuniform structures of FIGS. 7-9 are much more "isotropic." Whether anisotropic or isotropic, preferred structures for most applications have relatively narrow band gaps.

As an exemplary quasicrystalline embodiment, one may obtain a sequence of periodic approximants of a Penrose tiling pattern (or other purely random structure) of size L by replacing the golden mean in expressions for the lattice vectors and dot products by a ratio of integers, $\rho=F_{n+1}/F_n=$ (1/1, 2/1, 3/2, 5/3), where $F_n$ is the nth Fibonacci number. The unit cell in this non-limiting case is rectangle-shaped and its area grows as n increases and the rational approximant approaches $r=(\sqrt{5}+1)/2$. In tests for convergence as the approximant n increases, the optimal Penrose pattern for TM radiation alone is achieved by placing at each vertex a dielectric disk of radius r/a=0.177 (with a equal to the rhombus edge length of the underlying Penrose tiling). The TM band gap is $\Delta\omega/\omega_c=37.6\%$ (where $\Delta\omega$ is the gap width and $\omega_c$ is the value of the frequency at the midpoint of the gap), consistent with what has been previously reported (Rechtsman et al., Phys. Rev. Lett. 101: 73902, 2008). Next, one may construct a tessellation whose edges define a structure that produces a nearly optimal TE band gap. The optimal structure in this embodiment has dielectric material of width w/a=0.103 along each edge; the TE band gap is $\Delta\omega/\omega_c=42.3\%$. Although not intended to be limiting, the calculated TE band gap in this example is the largest ever reported for a quasicrystal lattice. Finally, for the complete band gap, the optimal structure is achieved by placing along each edge of trihedral intersection of the network a circular cylinder of radius r/a=0.157 and setting the cell wall thickness to w/a=0.042. The band gap results shown in FIG. 6 were obtained by means of a supercell approximation and a plane-wave expansion formalism. Preferably, the process of finding the optimum complete band gap includes convergence tests for dependence on system size, as illustrated by the plot in FIG. 6. Although not intended to be limiting, the resulting structure in this example displays a calculated complete (TM and TE) photonic band gap of 16.5%—the first complete band gap ever reported for a photonic quasicrystal with five fold symmetry and comparable to the largest band gap (20%) found for photonic crystals with the same dielectric contrast.

Although photonic crystals have larger complete band gaps (FIG. 5), quasicrystalline and disordered hyperuniform PBG materials offer advantages for many applications. First, both are significantly more isotropic, which is advantageous for use as highly-efficient isotropic thermal radiation sources and waveguides with arbitrary bending angle. Second, the properties of defects and channels useful for controlling the flow of light are different for crystal, quasicrystal and disordered structures. Quasicrystals, like crystals, have a unique, reproducible band structure; by contrast, the band gaps for the disordered structures have some modest random variation for different point distributions. On the other hand, due to their compatibility with general boundary constraints, photonic band gap structures constructed around disordered hyperuniform patterns can provide a flexible optical insulator platform for planar optical circuits. Moreover, eventual fabrication flaws that could seriously degrade the optical characteristics of photonic crystals and perhaps quasicrystals are likely to have less effect on disordered hyperuniform structures, therefore relaxing the fabrication constraints.

EXPERIMENTAL

Figure 10:
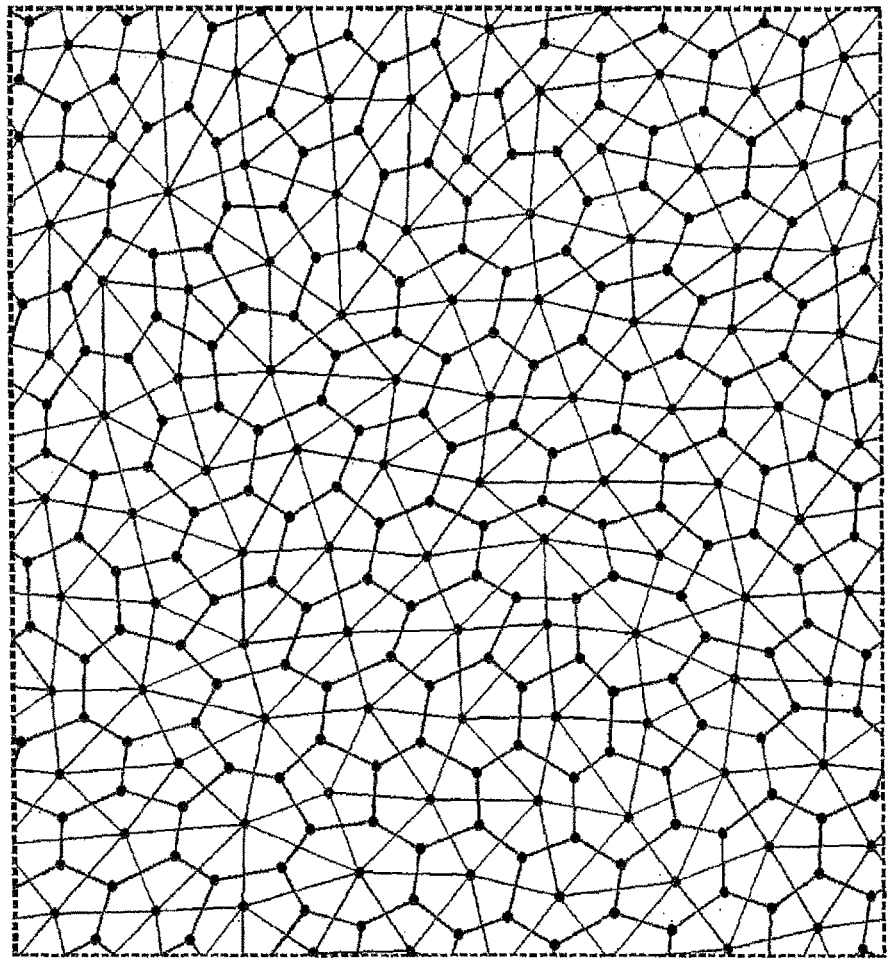
FIG. 10 shows a tessellation map of a disordered hyperuniform point pattern and (in FIG. 10 CONT.) a photograph of an actual heterostructure based on the map, fabricated from a dielectric polymer.
Figure 10:
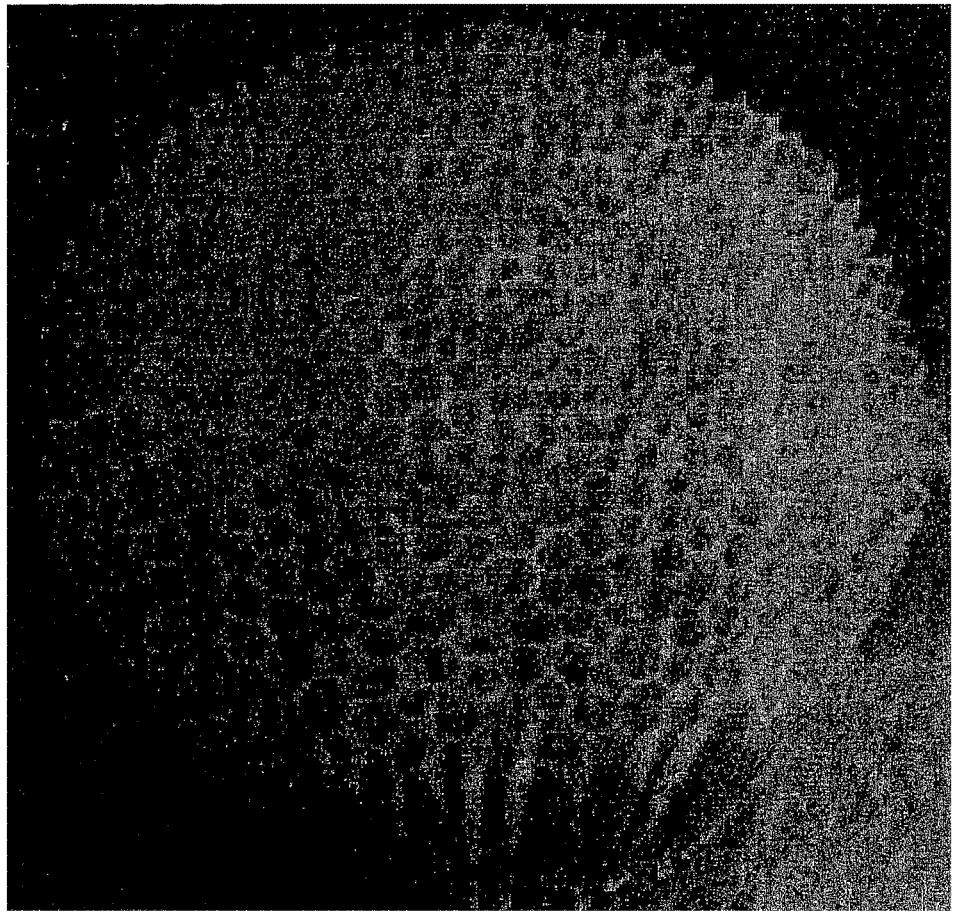

In FIG. 10, a photograph of a physical realization of a hyperuniform disordered photonic structure is presented (FIG. 10 CONT.). It was constructed from the tessellated point-pattern shown first in FIG. 10. The point-pattern and the layout of the cylinders in the tessellation of the point-pattern was developed according to the guidance provided hereinabove. The hyperuniform disordered photonic structure was fabricated by programming the co-ordinates for the cylinders in the pattern on the left into a rapid-prototyping stereolithography device (SLA-7000™, 3D Systems®, Rock Hill, S.C.) that produces a solid plastic model by ultraviolet laser polymerization. Accura 25™ (3D Systems®) was used as the pre-polymer. Programming and operation of the device was conducted according to the manufacturer's instructions. The Viper si2™, used with WaterClear Ultra 10122™ (3D Systems®) may also be used. The fabricated heterostructure is macroscopic, but the design can be miniaturized, e.g., for nanoparticles or other particles. For example, laser tweezers can be used for particle trapping or two-photon polymerization can be used. Such methods allow construction of a matrix of dielectric components with a photonic bandgap in the visible.

Transmission measurements for the heterostructure of FIG. 10 can be made with a HP Model 8510C Vector Analyzer in three bands, from 8 to 15, from 15 to 26 and from 26 to 42 GHz. To approximate plane waves, a single $TE_{10}$ mode is coupled through two sets of horn-attached waveguides with two custom-made polystyrene microwave lenses. Before the sample is put in, the transmission spectrum of the setup is recorded for normalization.

Figure 11:
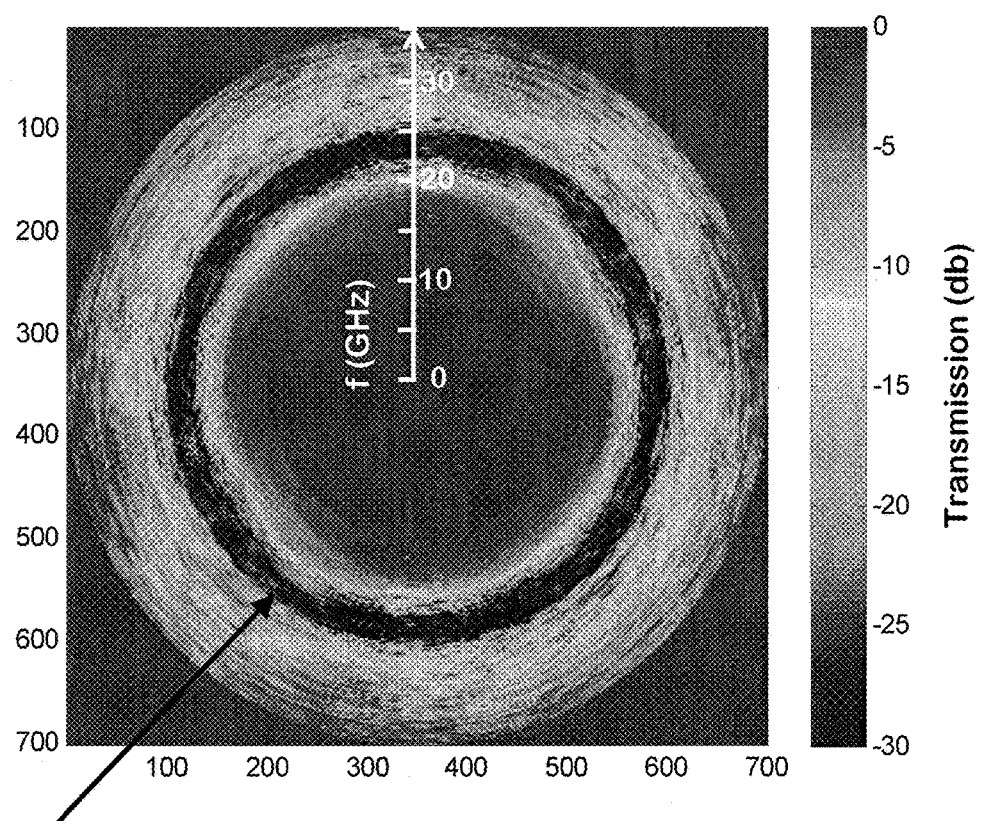
FIG. 11 is a photographic image of a pattern made by transmitting microwave radiation through the heterostructure shown in FIG. 10. The concentric ring identified by the arrow arises in the image because of a TE photonic band gap in the structure.

An image formed by microwaves transmitted through the structure in the photograph in FIG. 10 is reproduced in FIG. 11. The arrow-point identifies a TE band gap in the structure. Materials that confer higher dielectric contrast on the structure than the polymer material employed here are used to open a complete band-gap in the structure. As noted above, to accommodate a different electromagnetic regime (e.g., visible light), the structure is scaled down.

We claim:

1. A method of making a design that optimally blocks TE polarization, comprising:
    a) providing a two-dimensional point pattern in a hyperuniform, translationally disordered manner;
    b) constructing a Delaunay tiling from the said two-dimensional point pattern, said tiling comprising tiles;
    c) determining the centroid of each tile of said tiling;
    d) connecting the centroids that surround each point to transform the centroid point-pattern into a tessellation of cells, said cells comprising edges;
    e) decorating said cell edges with walls of dielectric material; and
    f) varying the width of the walls until the maximal TE band gap is obtained,
    wherein the design comprises a non-crystalline heterostructure comprising a plurality of disordered material-elements disposed hyperuniformly therein, without periodic or quasiperiodic translational order, in a condensed or solid state, said non-crystalline heterostructure being isotropic and having a complete band gap.

2. The method of claim 1, said walls comprise a trihedral network having vertices.

3. The method of claim 2, further comprising decorating said vertices of said trihedral network of said cell walls with circular cylinders, said cylinders having a radius.

4. The method of claim 3, further comprising varying the radius of said cylinders to achieve an optimal band gap.

* * * * *